(12) United States Patent
Soeldner et al.

(10) Patent No.: US 12,432,072 B2
(45) Date of Patent: ***Sep. 30, 2025

(54) METHOD FOR CONDUCTING A BIOPROCESS

(71) Applicant: Sartorius Stedim Biotech GmbH, Goettingen (DE)

(72) Inventors: Robert Soeldner, Goettingen (DE); Jonas Austerjost, Rietberg (DE); David James Pollard, Bohemia, NY (US)

(73) Assignee: Sartorius Stedim Biotech GmbH, Goettingen (DE)

( * ) Notice: Subject to any disclaimer, the term of this patent is extended or adjusted under 35 U.S.C. 154(b) by 277 days.

This patent is subject to a terminal disclaimer.

(21) Appl. No.: 18/029,327

(22) PCT Filed: Sep. 16, 2021

(86) PCT No.: PCT/EP2021/075494
§ 371 (c)(1),
(2) Date: Mar. 29, 2023

(87) PCT Pub. No.: WO2022/069243
PCT Pub. Date: Apr. 7, 2022

(65) Prior Publication Data
US 2023/0370281 A1    Nov. 16, 2023

(51) Int. Cl.
*H04L 9/32* (2006.01)
*H04L 9/00* (2022.01)

(52) U.S. Cl.
CPC .............. *H04L 9/3247* (2013.01); *H04L 9/50* (2022.05)

(58) Field of Classification Search
CPC ..... H04L 9/3247; H04L 9/50; H04L 2209/88; H04L 9/3239; H04L 63/123;
(Continued)

(56) References Cited

U.S. PATENT DOCUMENTS 8,719,576 B2   5/2014   Buldas et al.
8,846,383 B2   9/2014   Luttmann et al.
(Continued)

FOREIGN PATENT DOCUMENTS

| CN | 110675150 | 1/2020 |
| EP | 2565832 | 3/2013 |
| WO | 2022069243 | 4/2022 |

OTHER PUBLICATIONS

"European Search Report," for European Patent Application No. EP 20 19 9402 Mailed Mar. 9, 2021 (5 pages).
(Continued)

*Primary Examiner* — Javier O Guzman
(74) *Attorney, Agent, or Firm* — Pauly, DeVries Smith & Deffner LLC

(57) ABSTRACT

A method for conducting a bioprocess with a digital control unit of a bioprocess arrangement, wherein the digital control unit comprises a local data storage and a local processor unit, wherein bioprocess data are generated by the digital control unit. It is proposed, that in a data safety routine, a documentation routine and a signing routine are executed, that in the documentation routine, documentation data are generated from the bioprocess data and that in the signing routine, a cryptographic private key is extracted from private key data and the documentation data are digitally signed with the cryptographic private key by generating a digital signature and that the documentation routine is executed continuously during the bioprocess and that the signing routine is executed discontinuously during the bioprocess in several signing cycles according to a signing strategy, which defines trigger events for initiating the signing routine.

22 Claims, 4 Drawing Sheets

(58) Field of Classification Search
CPC ..... H04L 63/126; H04L 67/12; H04L 67/125; Y02P 90/30; G06F 21/606; G06F 21/645; G16H 10/40; G06Q 2220/00; G06Q 30/018; G06Q 50/04
See application file for complete search history.

(56) References Cited

U.S. PATENT DOCUMENTS

| | | | | |
|---|---|---|---|---|
| 10,956,549 | B2* | 3/2021 | Li | H04L 63/0861 |
| 2004/0039706 | A1* | 2/2004 | Skowron | G06Q 10/10 |
| | | | | 705/51 |
| 2007/0192715 | A1* | 8/2007 | Kataria | G06Q 10/087 |
| | | | | 705/28 |
| 2009/0019549 | A1* | 1/2009 | Reid | G06F 21/6209 |
| | | | | 726/27 |
| 2011/0066859 | A1* | 3/2011 | Iyer | H04W 12/106 |
| | | | | 713/181 |
| 2013/0278635 | A1* | 10/2013 | Maggiore | G06F 3/0304 |
| | | | | 345/633 |
| 2020/0134543 | A1* | 4/2020 | Pizzi | G06N 20/00 |
| 2020/0145219 | A1* | 5/2020 | Sebastian | H04L 9/50 |
| 2021/0095239 | A1* | 4/2021 | Recker | C12M 23/44 |

OTHER PUBLICATIONS

"International Search Report and Written Opinion," for PCT Application No. PCT/EP2021/075494 Mailed Dec. 22, 2021 (14 pages).
"Your Guide to Upstream Processing Solutions From Research to Production," Sep. 1, 2016, retrieved from the internet on Jan. 22, 2018, URL <https://www.connect-upstream.com/fileadmin/media/pdf/Cata_Upstream_S--1526-e.pdf> pp. 88, 89, 102-104 (108 pages).

* cited by examiner a)

b)

METHOD FOR CONDUCTING A BIOPROCESS

CROSS-REFERENCE TO RELATED APPLICATIONS

This application is a national stage application under 35 U.S.C. 371 of International Patent Application Serial No. PCT/EP2021/075494, entitled "Method for Conducting a Bioprocess," filed Sep. 16, 2021, which claims priority from European Patent Application No. EP 20199402.7, filed Sep. 30, 2020, the disclosure of which is incorporated herein by reference.

FIELD OF THE TECHNOLOGY

Various embodiments relate to a method for conducting a bioprocess, a digital control unit of a bioprocess arrangement for controlling a bioprocess, a control system, a data processing system, a computer program product and a computer readable storage media.

SUMMARY

The term "bioprocess" presently represents biotechnological and biopharmaceutical processes, which are involved in the manufacturing of desired therapeutic bioproducts such as biologics, vaccines, components for cell or gene therapy, or of non-therapeutic bioproducts such as pigments, biofuels or nutritional supplements. Such bioproducts can either be manufactured by living cells, or the cell itself might be the bioproduct, or the bioproduct can be the result of a cell free manufacturing based on cell components that are of either natural or non-natural origin.

The "bioprocess arrangement" comprises at least one device or the combination of two or more devices involved in the bioprocess, such as a bioreactor, a digital control unit (DCU), a filtration device, chromatography equipment, a centrifuge, a freeze dryer and analytical devices, which might be either single-use or multi-use equipment.

For at least partly automatically controlling a bioprocess, a method for conducting a bioprocess using a digital control unit comes into play. An example for such a digital control unit, which is the starting point for some embodiments, is shown in DE 102 37 082 A1. The known digital control unit comprises all electronic components to control the bioprocess, to receive sensor data and to communicate with the user via a user interface. This allows to execute a bioprocess control routine, in which bioprocess data are being generated in order to document the real life execution of the desired bioprocess.

The above noted bioprocess data are particularly important, for example, if a new pharmaceutical product is subject of a compliance procedure before its introduction into the market. Such compliance procedures often require proof, that the respective process in the bioprocess laboratory is in accordance with predefined rules. For instance during clinical trials this is of particular importance due to quality control standards and regulatory measures in clinical research, which are required by the respective national drug agency, such as the FDA, for the approval process of new drugs. However, this does not only concern such experimental phases, in which the documentation of process steps and sensor data is predominantly relevant, but also the manufacturing phase, in which the documentation of process quality plays an important role, according to GMP standards. GMP, or good manufacturing practice, are the practices required to conform to the guidelines recommended by agencies such as the FDA that control the authorization and licensing of the manufacture and sale of pharmaceutical products. These guidelines define the minimal manufacturing requirements that must be fulfilled in order to assure that the respective product is high in quality for their intended use. The accordance with GMP standards is overseen by regulatory agencies all over the world.

In any of the above noted cases, the integrity of the bioprocess data is necessary. This means that it has to be ensured that the bioprocess data have not been manipulated, be it willingly or unwillingly.

In order to ensure the integrity of the bioprocess data, it has been proposed to submit the respective data in online calendars and externally signing the data applying a generally known signing method (U.S. Pat. No. 8,719,576 B2). This known concept leaves room to when the respective bioprocess data are signed. This is not only an advantage, but also a drawback. With ensuring the data integrity in the above noted case, generally some drawbacks go along. The main drawback is, that the data acquisition during the bioprocess as well as the process of validating the data integrity by the recipient during the compliance procedure are becoming more complex. During or at the end of the bioprocess, signing has explicitly to be initiated and for validating the data integrity during the compliance procedure, the respective data set has to be validated using the respective digital signature. Now taking into account, that bioprocess data may be collected over a large amount of time by various, collaborating laboratory units, and that also the recipient of the bioprocess data, during the compliance procedure, may be structured in various recipient units, signing of the bioprocess data has come to be a complex management task with low efficiency overall.

It is an object of some embodiments to provide means that allow to increase efficiency with regard to the process of signing.

The above noted problem is solved for a method for conducting a bioprocess as described herein.

First of all, it has been found out that signing is to be done in several signing cycles during the bioprocess based on a predefined signing strategy. The result is a segmentation of the bioprocess data in bioprocess data sets, which are each signed in the respective signing routine. Second, it has been found out that this segmentation may easily be adapted to the bioprocess and/or to the particular needs of the recipients, increasing efficiency for later processing of the bioprocess data.

It is proposed to implement a signing strategy, according to which the signing routine is automatically initiated in various signing cycles. This includes defining trigger events for initiating the signing routine, which leads to a particularly simple implementation.

The digital control unit, which is at least partly executing the proposed method, comprises a local data storage and a local processor unit, which presently are to be considered the core components for digital data processing. Parts of the proposed method may well be executed by external components. Parts of the proposed method, in particular the signing routine, may also be initiated by the digital control unit, possibly to be executed by an external unit.

The expression "external" throughout this document means a unit or step located or executed outside the digital control unit.

The expression "initiate" with respect to a routine means that the execution of the routine is being started immediately or with a certain time lag. In any case, the initiation of a routine always leads to the subsequent execution of the routine.

The digital control unit, according to some embodiments, generates bioprocess data, which serve to describe the bioprocess as will be explained. These bioprocess data are the basis for the documentation, which is needed for above noted compliance procedures.

In detail, private key data are stored in the digital control unit or any other unit such as an external signing unit, which is the basis for the execution of a data safety routine. The local processor unit may at least initiate this data safety routine, such that the control of the whole data safety routine stays within the local processor unit.

In the data safety routine, a documentation routine is executed. In the documentation routine, documentation data are generated from the bioprocess data. These documentation data are subject to signature to be explained in the following.

A signing routine is initiated in the data safety routine. In the signing routine, a cryptographic private key is extracted from the private key data. The documentation data are then digitally signed with the cryptographic private key by generating a digital signature. In short, in the signing routine a digital signature of the documentation data is performed based on asymmetric cryptography, which as such is well known from the state of the art. With the signing routine being executed in a trusted unit, a high level of safety in view of data integrity may be achieved, as far as the signing routine as such is concerned.

The above noted extraction of the cryptographic private key from the private key data is particularly simple, if the private key data include the cryptographic key or are even identical to the cryptographic private key. However, the extraction may be more complex. For example, the cryptographic private key may be derived from the private key data based on an unpredictable random number.

As the data safety routine may be designed, such that very little data processing is needed for generating the documentation data, the proposed solution may be realized with a wide range of existing digital control units without even adding any additional hardware. This is not only a cost advantage, but also facilitates the introduction of the proposed solution into existing laboratories.

For the realization of the proposed solution, the documentation routine is executed continuously during the bioprocess and that the signing routine is executed discontinuously during the bioprocess in several signing cycles according to a signing strategy, which defines trigger events for initiating the signing routine.

The expression "continuously" with respect to the documentation routine means that the documentation routine, after its initiation, is continuously generating bioprocess data. The expression "discontinuously" with respect to the signing routine means that the digital signature is only being generated on the occurrence of the above noted trigger events.

According to various embodiments, the digital control unit further comprises a bioprocess interface for sending and receiving bioprocess control data, which bioprocess interface comprises an actuator interface for sending actuator data to at least one actuator for influencing the bioprocess and a sensor interface for receiving sensor data related to the bioprocess from at least one sensor. For instance, a stirrer or a valve could be such actuators, while the associated, respective actuator data could be the stirring frequency in rounds per minute (rpm), or the fluid flow in milliliter per minute (mL/min), respectively. Exemplary sensors could be the biomass sensor, pH sensor or oxygen sensor, reflecting the respective data. According to this embodiment, also, the digital control unit comprises a user interface for displaying to a user at least part of the bioprocess data and for receiving user control command data. Especially in the experiment phase, the user interface provides one possibility for the user to influence the bioprocess during both, the experimental development phase as well as the manufacturing phase. Common, exemplary parameters that are set by the user are stirring speed, temperature, pH, oxygen saturation and the like.

According to various embodiments, the digital control unit is configured to execute a bioprocess control routine via the local processor unit to control the bioprocess. Here, all automation, if needed, takes place. In the bioprocess control routine, the digital control unit receives the sensor data from the sensor. In addition, in the bioprocess control routine, the digital control unit generates the actuator data based on the user control command data and/or the sensor data and controls the actuator by sending the actuator data to the actuator thereby influencing the bioprocess. This control may be based on a simple logic operation between the user control command data and/or the sensor data to derive the actuator data. It may also be based on a control loop, that derives actuator data in order to reach a certain target value. Finally, it may be based on a sequence control, that is usually realized by a software noted below. Accordingly, the digital control unit may provide a coordination function for the whole bioprocess on the one hand, and may also be only an execution tool to execute requests from at least one other control unit on the other hand.

In the bioprocess control routine, the digital control unit also generates the bioprocess data from the actuator data and/or the sensor data and/or the user control command data.

Various embodiments are directed to signing strategies, which are mainly based on trigger events related to the bioprocess itself. According to various embodiments, at least one trigger event is defined as an event directly related to the bioprocess. The expression "directly" means, that the respective trigger event is based on information, which is inherent to the bioprocess. Examples are changes in bioprocess steps, bioprocess phases and bioprocess states. With the trigger events being directly related to the bioprocess, the probability is high, that the segmentation of the bioprocess data into signed bioprocess data sets is performed in a practical way regarding later compliance procedures.

According to various embodiments, in the documentation routine, the bioprocess data are grouped into data blocks, which data blocks are then processed in a step of hashing. According to various embodiments, the data blocks are being hashed in form of a tree structure such as a Merkle tree structure. The signing of those documentation data, which may include the complete hash tree structure or which may also include only the hash root, in any case require only little data processing as noted above.

Various embodiments clarify, that during the bioprocess the digital control unit works continuously receiving the sensor data from the sensor in the bioprocess control routine and also continuously sending actuator data to the actuator thereby influencing the bioprocess. This allows for the bioprocess control routine to realize control strategies such as feedback strategies with control loops in close to real time.

As noted above, the segmentation of the bioprocess data into bioprocess data sets result from the definition of trigger events. These bioprocess data sets are the basis for the signing routine according to some embodiments. In some embodiments, subsequent bioprocess data sets are related to each other in a predefined way. This may be an overlapping of subsequent bioprocess data sets or including an identifier of the respective previous bioprocess data set. In this way it is ensured, that no data between two subsequent bioprocess data sets are being missed in the signing routine.

The digital signature generated based on the documentation data may be stored in the local data storage of the digital control unit. It may also be stored in any other data storage, that is connected to the digital control unit via a data transmission interface. Both possibilities are subject to the clarification that after executing the signing routine, unnoticed manipulation of the bioprocess data is not possible as noted above, such that the location of storage of the digital signature does not play any role.

Various embodiments are directed to variants regarding the initiation and execution of the signing routine. While according to some embodiments, the digital control unit is initiating and executing the complete signing routine, according to some embodiments, the digital control unit is merely initiating the signing routine to be executed by an external signing unit. The expression "to be executed" in this context means that the above noted initiation is performed such that the respective routine, here the documentation routine, is being executed by the respective external unit, here the documentation unit. For this, within the initiation, for example a request may be transmitted from the initiating unit, here the local processor unit, to the executing unit, here the documentation unit, via a data connection.

In both cases, the digital control unit stays in control of the signing routine, ensuring, that the signing routine may easily be synchronized with the bioprocess via the above noted trigger events.

According to various embodiments, the proposed digital control unit is provided as such, which is configured to perform the above noted, proposed method for conducting a bioprocess. Reference may be made to all explanations given with regard to the proposed method.

Various embodiments are directed to a control system with a proposed digital control unit and an external documentation unit and/or an external signing unit to execute the above noted, proposed method. Again, reference may be made to all explanations given with regard to the proposed method.

Various embodiments are directed to the data processing system for the realization of the proposed method, in particular for the realization of the respective routines. In some embodiments, this data processing system comprises at least the local data storage and the local processor unit of the digital control unit. All explanations given with regard to the proposed digital control unit are again fully applicable to the proposed data processing system.

According to various embodiments, a computer program product for the proposed data processing system is provided as such. The computer program product is configured to realize the proposed method, in particular, to realize the above noted routines. Again, all explanations given for the proposed method are fully applicable to the proposed computer program product.

According to various embodiments, a computer readable storage media, on which the computer program is stored, is provided as such. Again all explanations given for the proposed method are fully applicable to the proposed readable storage media.

Finally, the proposed bioprocess arrangement shall be able to be provided as such. The bioprocess arrangement can include a bioreactor and all components and/or devices performing the corresponding upstream- and downstream processing phases.

The upstream processing phase of a bioprocess generally consists of all actions and workflows from the development, optimization, screening and selection of a strain or cell line to its cultivation and the manufacturing of the desired bioproduct by the cell or cell components. This cultivation can be performed in various scales (microliter scale to several thousands of liters scale) using different reactor setups and geometries (rocking motion, stirred tank, bubble column, fixed bed, etc.) by applying different modes of operation (batch, fed-batch, continuous, in particular perfusion, or combinations thereof). The cultivation is usually monitored, analyzed and controlled based on different sensor technologies (soft, electrochemical, biochemical, optical, etc.; offline, online, inline, at line). Typically, after the manufacturing of a desired bioproduct, it is purified. Here, the cultivation broth is separated from the desired bioproduct (e. g. monoclonal antibodies, polyketides, enzymes, vaccines).

The downstream processing phase of a bioprocess generally includes various techniques and methods for recovery, purification, analysis and characterization of the desired bioproduct. It involves methods, such as cell disruption, sedimentation, centrifugation, precipitation, crystallization, extraction, filtration, adjustment of pH and conductivity of liquids, enzymatic or chemical modification, dilution, buffer exchange, evaporation, adsorption and chromatography. Analysis and characterization steps may be included to ensure the purified bioproduct is compliant to critical quality attributes (e.g. glycosylation patterns of antibodies, concentration of endotoxins). A final formulation step, which involves buffer exchange, drying, freeze-drying or crystallization, might be performed to bring the purified bioproduct in a suitable state for storage and distribution before it is filled and packaged.

Another variant includes an arrangement performing an upstream process, which is continuously connected to a downstream arrangement.

All explanations given regarding the proposed process, the proposed digital control unit, the proposed control system, the proposed data processing system, the proposed computer program product and the proposed computer readable storage media are fully applicable to the bioprocess arrangement.

Various embodiments provide a method for conducting a bioprocess with a digital control unit of a bioprocess arrangement, wherein the digital control unit comprises a local data storage and a local processor unit, wherein bioprocess data are generated by the digital control unit, wherein in a data safety routine, a documentation routine) and a signing routine are executed, that in the documentation routine, documentation data are generated from the bioprocess data and that in the signing routine, a cryptographic private key is extracted from private key data and the documentation data are digitally signed with the cryptographic private key by generating a digital signature, that the documentation routine is executed continuously during the bioprocess and that the signing routine is executed discontinuously during the bioprocess in several signing cycles according to a signing strategy, which defines trigger events for initiating the signing routine.

In various embodiments, the digital control unit comprises a bioprocess interface for sending and receiving bioprocess control data, that the bioprocess interface comprises an actuator interface for sending actuator data to at least one actuator for influencing the bioprocess, that the bioprocess interface comprises a sensor interface for receiving sensor data related to the bioprocess from at least one sensor, that the digital control unit comprises a user interface for displaying to a user at least part of the bioprocess data and for receiving user control command data.

In various embodiments, a bioprocess control routine is executed by the local processor unit to control the bioprocess, that in the bioprocess control routine, the sensor data are received by the digital control unit from the sensor, that in the bioprocess control routine, the actuator data are generated by the digital control unit based on the user control command data and/or the sensor data and the actuator is controlled by the digital control unit by sending the actuator data to the actuator thereby influencing the bioprocess, that in the bioprocess control routine, the bioprocess data are generated by the digital control unit from the actuator data and/or the sensor data and/or the user control command data.

In various embodiments, at least one trigger event is defined as an event directly related to the bioprocess.

In various embodiments, the bioprocess is assigned bioprocess steps and/or is assigned bioprocess phases and/or is assigned bioprocess states, and that at least one trigger event is defined with relation to at least one bioprocess step and/or at least one bioprocess phase and/or at least one bioprocess state.

In various embodiments, at least one trigger event is defined in a time based manner.

In various embodiments, at least one trigger event is defined as a point in time relative to a bioprocess step.

In various embodiments, at least one trigger event is defined as a periodically repeating trigger event with a predefined period in terms of time.

In various embodiments, at least one trigger event is defined based on a predefined change in the bioprocess phase and/or the bioprocess state.

In various embodiments, at least one trigger event is defined based on a start or a termination of a bioprocess step or based on a start or a termination of a bioprocess phase.

In various embodiments, at least one trigger event is defined based on the bioprocess control data.

In various embodiments, at least one trigger event is defined based on the sensor data and/or the user control command data and/or the actuator data.

In various embodiments, the documentation routine comprises a step of grouping the bioprocess data into data blocks and a step of hashing the data blocks generating hashes of the data blocks and that the documentation data are generated from the hashes of the data blocks.

In various embodiments, the documentation routine comprises a step of hashing the hashes of the data blocks in form of a tree structure, in particular a Merkle tree structure, into a hash root and that the documentation data are generated from the hash root.

In various embodiments, during a single bioprocess the digital control unit continuously receives the sensor data from the sensor in the bioprocess control routine and continuously sends actuator data to the actuator thereby influencing the bioprocess.

In various embodiments, each signing routine is based on an assigned bioprocess data set.

In various embodiments, subsequent bioprocess data sets are overlapping each other, and/or, that an identifier of a respective previous bioprocess data set is added to the respective subsequent bioprocess data set.

In various embodiments, the digital signature generated by signing the documentation data is received from the digital control unit via the bioprocess interface, in particular a data transmission interface, and stored in the local data storage, and/or, that the digital control unit initiates the transmission of the digital signature and/or the documentation data and/or the bioprocess data or parts of the respective data to an external data storage, in particular a laboratory process control system, via the data transmission interface.

In various embodiments, the private key data are stored in the local data storage, that the data safety routine is executed by the local processor unit, that the documentation routine is executed by the local processor unit in the data safety routine, that in the documentation routine, the documentation data are generated from the bioprocess data by the digital control unit, that the signing routine is executed by the local processor unit in the data safety routine and that in the signing routine, cryptographic private key is extracted from the private key data by the digital control unit and that the documentation data are signed with the cryptographic private key by the digital control unit by generating a digital signature.

In various embodiments, the private key data are stored in an external signing unit, that the data safety routine is initiated by the local processor unit, that the documentation routine is initiated by the local processor unit in the data safety routine to be executed by the local processor unit or an external documentation unit, that in the documentation routine, documentation data are generated from the bioprocess data by the local processor unit or the external documentation unit, that the signing routine is initiated by the local processor unit in the data safety routine to be executed by an external signing unit and that in the signing routine, a cryptographic private key is extracted from the private key data by the external signing unit and that the documentation data are digitally signed with the cryptographic private key by generating a digital signature.

Various embodiments provide a digital control unit of a bioprocess arrangement for controlling a bioprocess, wherein the digital control unit comprises a local data storage and a local processor unit, wherein the digital control unit comprises a bioprocess interface for sending and receiving bioprocess control data, wherein the bioprocess interface comprises an actuator interface for sending actuator data to at least one actuator for influencing the bioprocess, wherein the bioprocess interface comprises a sensor interface for receiving sensor data related to the bioprocess from at least one sensor, wherein the digital control unit generates bioprocess data, wherein the digital control unit comprises a user interface for displaying to a user at least part of the bioprocess data and for receiving user control command data, wherein the digital control unit is configured to execute a bioprocess control routine via the local processor unit to control the bioprocess, wherein in the bioprocess control routine, the digital control unit receives the sensor data from the sensor, wherein in the bioprocess control routine, the digital control unit generates the actuator data based on the user control command data and/or the sensor data and controls the actuator by sending the actuator data to the actuator thereby influencing the bioprocess, wherein in the bioprocess control routine, the digital control unit generates the bioprocess data from the actuator data and/or the sensor data and/or the user control command data, wherein private key data are stored in the local data storage unit or an external signing unit, that the digital control unit is configured to initiate a data safety routine via the local processor unit, that the digital control unit is configured to initiate a documentation routine via the local processor unit in the data safety routine to be executed by the local processor unit or an external documentation unit, that in the documentation routine, the local processor unit or the external documentation unit generates documentation data from the bioprocess data, that the digital control unit is configured to initiate a signing routine via the local processor unit in the data safety routine to be executed by the local processor unit or an external signing unit and that in the signing routine, the local processor unit or the external signing unit extracts a cryptographic private key from the private key data and digitally signs the documentation data with the cryptographic private key by generating a digital signature and that the documentation routine is executed continuously during the bioprocess and that the signing routine is executed discontinuously during the bioprocess in several signing cycles according to a signing strategy, which defines trigger events for initiating the signing routine and that the digital control unit is configured to initiate the signing routine discontinuously.

Various embodiments provide a control system with a digital control unit according to the disclosure and an external documentation unit and/or an external signing unit to execute a method according to the disclosure.

Various embodiments provide a data processing system for realizing the method according to the disclosure.

Various embodiments provide a computer program product for the data processing system according to the disclosure.

Various embodiments provide a computer readable storage media, on which the computer program product according to the disclosure is stored, such as in a non-volatile manner.

BRIEF DESCRIPTION OF THE DRAWINGS

In the following, an embodiment is explained with respect to the drawings. The drawings show FIG. 1 a proposed digital control unit of a proposed control system for executing a proposed method for conducting a bioprocess, FIG. 2 the working principle of the digital control unit according to FIG. 1 including a bioprocess control routine and a data safety routine, FIG. 3 an overview of trigger events according to signing strategies according to the method of FIG. 2, FIG. 4 a hash tree structure a) as generated in the data safety routine according to FIG. 2 and b) a respective hash tree structure based on manipulated bioprocess data.

DETAILED DESCRIPTION

The proposed digital control unit 1 of a bioprocess arrangement 2 serves for controlling a bioprocess such as a cultivation process of microorganisms or mammalian cells using a bioreactor 3 and components for the corresponding upstream- and downstream process (not displayed).

Figure 1:
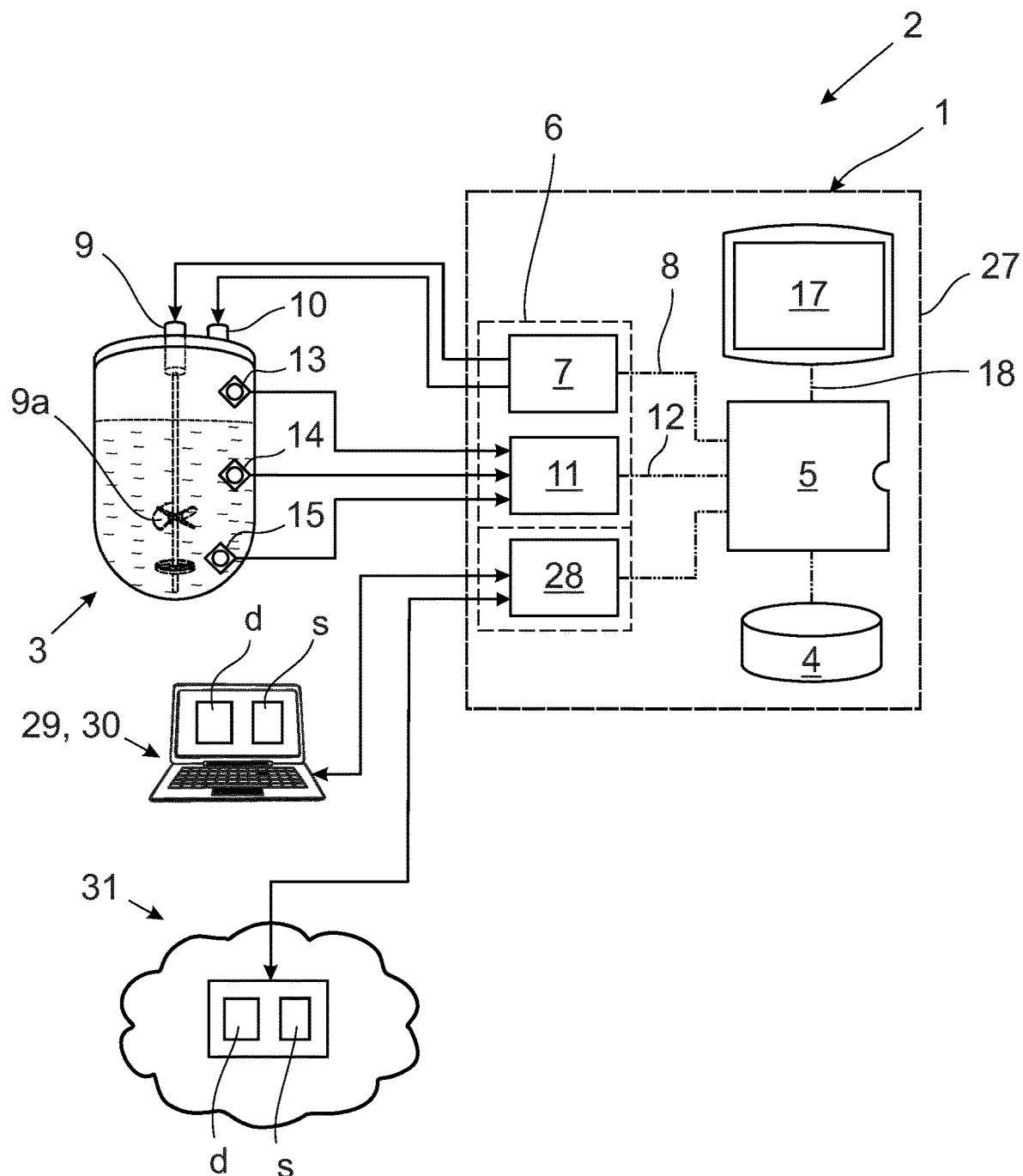

As shown in FIG. 1, the digital control unit 1 comprises a local data storage 4 and a local processor unit 5 for data processing. Both units 4, 5, namely the local data storage 4 and the local processor unit 5, are realized as electronic components. It may be pointed out, that the local processor unit 5 can include only one data processor, which performs all functions of the digital control unit 1. However, it may be provided, that the local processor unit 5 comprises more than one data processor, that interact with each other in order to perform all functions of the digital control unit 1.

As shown in FIG. 1, the digital control unit 1 comprises a bioprocess interface 6 for sending and receiving bioprocess control data. In particular, the bioprocess interface 6 comprises an actuator interface 7 for sending actuator data 8 to at least one actuator 9, 10 for influencing the bioprocess. The actuator 9, 10 is to be understood as any component, that may be controlled to be actuated, in order to influence the bioprocess. Here, the actuator 9 is a stirrer comprising an impeller 9a within the bioreactor 3, while the actuator 10 can be a valve for introducing fluid, such as a nutrient solution, into the bioreactor 3. Other possible actuators are pumps, liquid handling units, heating and/or cooling systems, or the like. It may be pointed out that the bioprocess arrangement 2 may comprise any number of actuators 9, 10 that each may be controlled by the actuator data 8. Furthermore, the bioprocess arrangement is not limited to upstream devices.

The bioprocess interface 6 also comprises a sensor interface for receiving sensor data 12 related to the bioprocess from at least one sensor 13, 14, 15. Such sensor 13, 14, 15 may be any sensor relevant to describe the bioprocess such as the biomass sensor, pH sensor or oxygen sensor, or the like. The function of those sensors may well be provided by soft sensors, that are also called virtual sensors. Soft sensors derive sensor values from other sensing sources based on a data model. Depending on the application, there are various possibilities to realize the necessary data processing hardware assigned to the respective soft sensor.

A sensor 13, 14, 15 in the above noted sense may be provided with its own sensor interface, that allows its connection to the bioprocess interface 6, such as its sensor interface 11, for the transfer of sensor data 12. Depending on its working principle, the sensor 13, 14, 15 may be connected to the sensor interface 11 of the bioprocess interface 6 for example via an electric, an optic, a pneumatic or a hydraulic connection. In the embodiment shown in FIG. 1 and only as an example, an electric connection is indicated. Again, the bioprocess arrangement 2 may comprise any number of sensors 13, 14, 15, which each provide sensor data to the digital control unit 1.

The digital control unit 1 generates bioprocess data 16, that serve to describe the bioprocess and that will be described in the following. The bioprocess data 16, just after their generation, are adding up to a continuous data stream S shown in FIG. 2.

The digital control unit 1 also comprises a user interface 17 for displaying to a user at least part of the bioprocess data 16 and for receiving the user control command data 18. Those user control command data 18 may be a command to start and terminate the bioprocess and/or to set certain control parameters such as the stirring speed of the impeller 9a, which the actuator 9 is assigned to.

Figure 2:
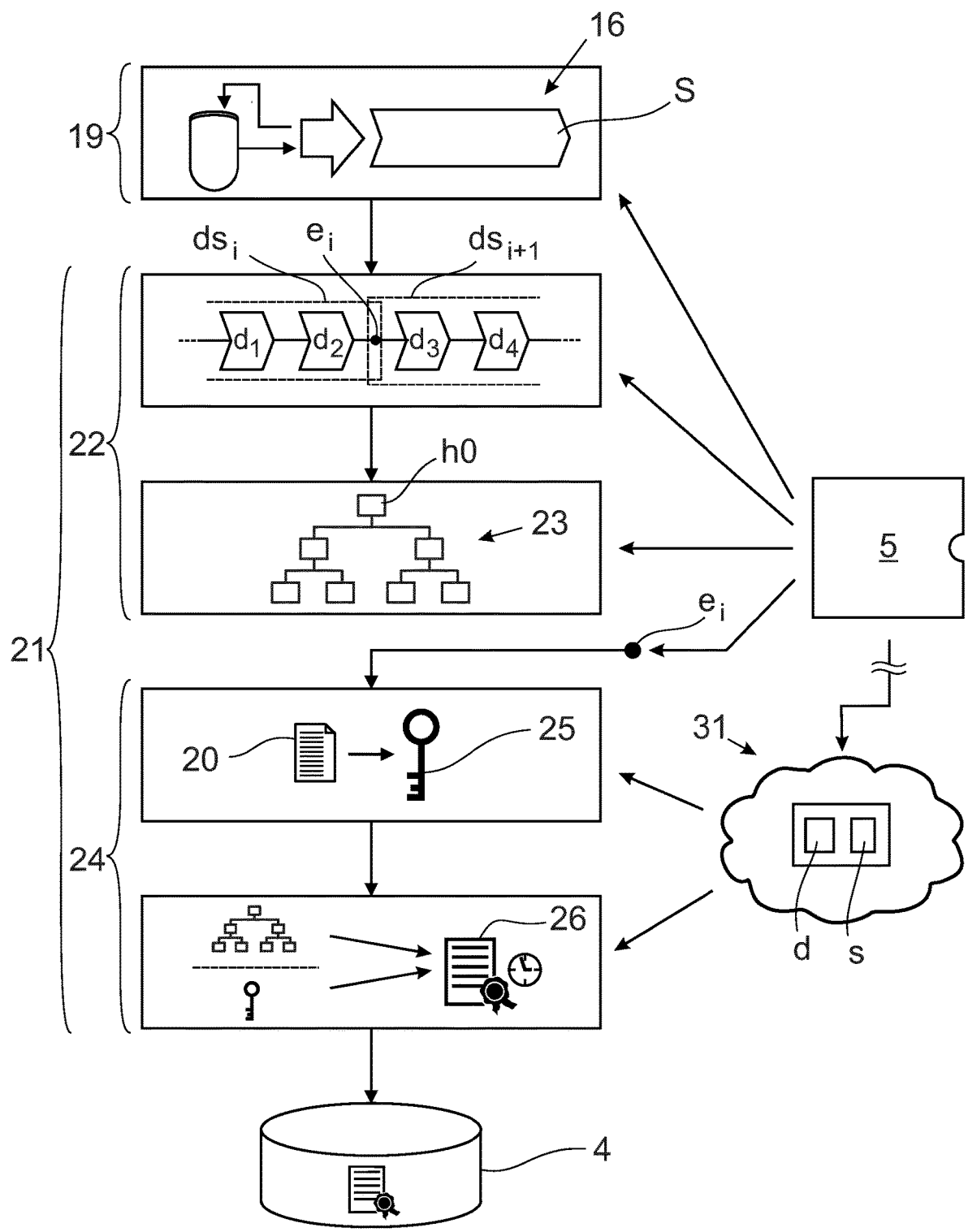

Further, the digital control unit 1 is configured to execute a bioprocess control routine 19 via the local processor unit 5 to control the bioprocess. This is indicated in FIG. 2 as well. In the bioprocess control routine 19, the digital control unit 1 receives the sensor data 12 from the respective sensor 13, 14, 15. In the bioprocess control routine 19, the digital control unit 1 also generates the actuator data 8 based on the user control command data 18 and/or the sensor data 12 and controls the actuator 9, 10 by sending the actuator data 8 to the actuator 9, 10 thereby influencing the bioprocess. From the actuator data 8 and/or the sensor data 12 and/or the user control command data 18, in the bioprocess control routine 19, the digital control unit 1 generates the bioprocess data 16.

The bioprocess control routine 19 can be based on a control software running on the local processor unit 5, which may be structured as a sequence program, which may include rules to control the actuator 9, 10, control loops or the like.

As noted above, according to some embodiments, data integrity with respect to the bioprocess data 16 is ensured by applying asymmetric cryptography, which can be controlled by the digital control unit 1 and which can be executed by an external signing unit s. For this, first of all, private key data 20 are stored either in the local data storage 4 or in the external signing unit s. Second of all, the digital control unit 1 is configured to initiate a data safety routine 21 via the local processor unit 5. The data safety routine 21 is relying on a safety software, which can run on the local processor unit 5 as well.

The safety routine 21 includes a documentation routine 22. In detail, the digital control unit 1 is configured to initiate the documentation routine 22 by the local processor unit 5 within the data safety routine 21, which documentation routine 22 is executed by the local processor unit 5 or an external documentation unit d. In this documentation routine 22, documentation data 23 are generated from the bioprocess data 16 by the local processor unit 5 or an external documentation unit d, which documentation data 23 are subject to digital signing.

It is possible for some embodiments that the data safety routine 21 includes a signing routine 24. Accordingly, the digital control unit 1 can be configured to initiate the signing routine 24 to be executed, in some embodiments, by the external signing unit s in the data safety routine 21. In the signing routine 24, a cryptographic private key 25 is extracted from the private key data 20 by the external signing unit s and the documentation data 23 are then signed with the cryptographic private key 25 by generating a digital signature 26.

The documentation routine 22 is executed continuously during the bioprocess, while the signing routine 24 is executed discontinuously during the bioprocess in several signing cycles according to a signing strategy P, which defines trigger events $e_i$ for initiating the signing routine 24. The signing strategy P is only indicated in FIG. 3 as the respective group of trigger events $e_i$. Each trigger event $e_i$ results in the initiation of a signing routine 24. This is indicated in FIG. 2.

Here, the digital control unit 1 has a casing 27, which should be robust in order to prevent manipulation. As an alternative or in addition, the digital control unit 1 is a mobile unit that can be moved with the local processor unit 5 and the local data storage 4 through a laboratory. Again as an alternative or in addition, it is provided, that the local processor unit 5 and the local data storage 4 are connected via, here electrical, cables and/or short range wireless communication to the sensor 13, 14, 15 and/or the actuator 9, 10. Again, as an alternative or in addition, the user interface 17 may well comprise a user display and a user input device, in particular a touch screen, each of which are located in or on the casing 27 of the digital control unit 1.

In some embodiments, the digital signature 26 generated by signing the documentation data 23 is stored in the local data storage 4. The digital control unit 1, as an alternative or in addition, may comprise a data transmission interface 28, wherein the digital control unit 1 transmits the digital signature 26 and/or the documentation data 23 and/or the bioprocess data 16 or parts of the respective data to an external data storage 29, which generally may be a process control system, which itself may well be another digital control unit. Here, the external data storage 29 is a so called "multifermenter" control system (MFCS), which comprises a local processor unit and a local data storage itself. The MFCS also provides a centralized process management system, dispatching requests to the digital control unit 1, which, however, does not play a role for this particular embodiment.

In some embodiments, the external documentation unit d and/or the external signing unit s is provided by a laboratory process control system 30 or a cloud service instance 31. Both alternatives are displayed in FIG. 1, while in FIG. 2, only the alternative of the documentation unit d and/or the signing unit s being provided by a cloud service instance 31 is displayed. This shows the high degree of flexibility in view of realization the signing routine 24.

It can be that the data connection between the digital control unit 1 on the one side and the external documentation unit d and/or the external signing unit s on the other side is realized using a message authentication code (MAC). This not only encrypts the relevant data, but also ensures data integrity. The latter may be realized by separately signing the relevant data by the digital control unit 1 with a cryptographic private key stored in the local data storage 4, before transmitting those data to the external signing unit s.

For the definition of the above noted trigger events $e_i$, multiple variants may be advantageous depending on the specific application.

In some embodiments, at least one trigger event $e_i$ is defined as an event directly related to the bioprocess. In particular, this may regard the bioprocess being assigned bioprocess steps $w_i$ and/or bioprocess states and/or bioprocess phases. This basic structure of a bioprocess may be derived in different variants from the representation of FIG. 3. While FIG. 3a) shows a sequence of bioprocess steps, FIG. 3b), 3c) each show diagrams, that represent a variable m, here the biomass per volume m, with respect to time t. Thereby, FIG. 3b), 3c) represent bioprocess phases and states, as will be explained.

As shown in FIG. 3a), at least one trigger event $e_i$ is defined with relation to at least one bioprocess step. In an embodiment according to FIG. 3a), such bioprocess steps $w_i$ can be the equilibration step and/or sample injection step and/or washing step and/or elution step of a chromatography column used in the downstream-process phase. It can be that at least one trigger event $e_i$ is defined as the change from one bioprocess step $w_i$ to another.

In various embodiments, at least one trigger event ei is defined in a time based manner, wherein, in some embodiments, at least one trigger event ei is defined as a point in time relative to a bioprocess step. It may also be advantageous to define at least one trigger event ei as a periodically repeating trigger event ei with a predefined period in terms of time. This can be in case of periodically reoccurring bioprocess steps and/or in strictly regulated production standard operation protocols.

In various embodiments, at least one trigger event $e_i$ is defined as a change between bioprocess phases. Such bioprocess phases can be, as shown in FIG. 3b) as an example, a batch cultivation phase and/or fed-batch cultivation phase and/or continuous cultivation phase and/or any other cell cultivation phase in a bioreactor.

In various embodiments, the respective trigger events $e_i$ can be defined as a change in bioprocess states. Here, at least one trigger event $e_i$ is defined as the change from one bioprocess state to another. As shown in FIG. 3c), such bioprocess states may be cell growth states, including but not limited to lag state, log state, stationary state and death state or any other state within bacterial or fungal fermentation processes or mammalian cell cultivation or any other cultivation of cells in a bioreactor.

As shown in FIG. 3a), at least one trigger event $e_i$ may be defined based on a start or a termination of a bioprocess step $w_i$ as for example the start or termination of a protein purification step using a chromatography column. As shown in FIG. 3b), at least one trigger event $e_i$ may be defined based on a start or a termination of a bioprocess phase. The latter can be the start or termination of batch-cultivation and/or fed-batch cultivation and/or continuous cultivation of cells.

Finally, at least one trigger event $e_i$ may be defined based on the bioprocess control data, here the sensor data and/or the user control command data and/or the actuator data. This also applies to the variants shown in FIGS. 3b) and 3c). One example might be the adjustment of at least one actuator 9, 10, such as the stirrer, which is regulated by control command data 18 by the user given via the bioprocess user interface 17. In case, the oxygen partial pressure decreases below a critical predefined threshold, this can for instance be necessary, in order to re-establish the for the bioprocess required oxygen level.

As indicated in FIG. 2, the documentation routine 22 comprises a step of grouping the bioprocess data 16 into data blocks $d_i$ and a step of hashing the data blocks $d_i$ generating hashes $h_i$ of the data blocks $d_i$, wherein the documentation data 23 are generated from the hashes $h_i$ of the data blocks $d_i$. In some embodiments, the documentation routine 22 comprises a step of hashing the hashes $h_i$ of the data blocks $d_i$ in form of a tree structure applying a standard hash function. The resulting hash tree His shown in FIG. 4a). In some embodiments, this tree structure is a Merkle tree structure.

It can be that the data blocks $d_i$ are hashed in form of a tree structure into a hash root h0, wherein the documentation data 23 are generated from the hash root h0. In a particularly simple variant, the documentation data 23 are identical to the hash root h0.

An important advantage of the above noted hashing is the fact that any and all amendments of the data blocks $d_i$ will lead to a corresponding amendment of the hash root h0, such that any amendment in the data blocks $d_i$ after hashing may easily be detected. A further advantage is the fact that it is only the hash root h0, that has to be introduced into the documentation data 23, which leads to easy data handling with low data processing requirements.

For the above noted hashing, various algorithms may be applied. Here, the hash algorithms "SHA-1", "SHA-2", "BLAKE2" may be applied. For the above noted signing, such as, an elliptic curve digital signature algorithm, in particular the signature algorithm "ECDSA", may be applied.

In order to reduce the opportunity for manipulating the bioprocess data 16 as much as possible, the documentation routine 22 may be executed, such as by the digital control unit 1, during control of the bioprocess in the bioprocess control routine 19. This may also be done by the external signing unit s as noted above.

Here, during at least part of the single bioprocess, the digital control unit 1 continuously receives the sensor data 12 from the sensor 13, 14, 15 in the bioprocess control routine 19 and continuously sends actuator data 8 to the actuator 9, 10 thereby influencing the bioprocess. The term "continuously" here generally means, that the respective actions, here the reception of sensor data 12 and the sending of actuator data 8, are being ongoingly and systematically, such as periodically, repeated.

Figure 3:
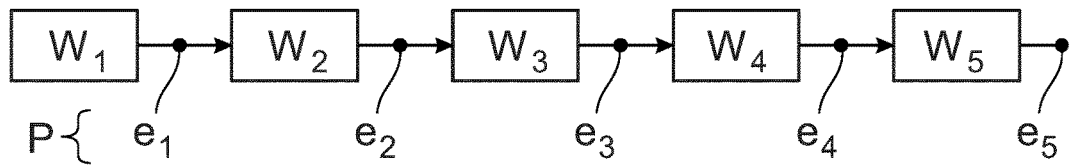
Figure 3:
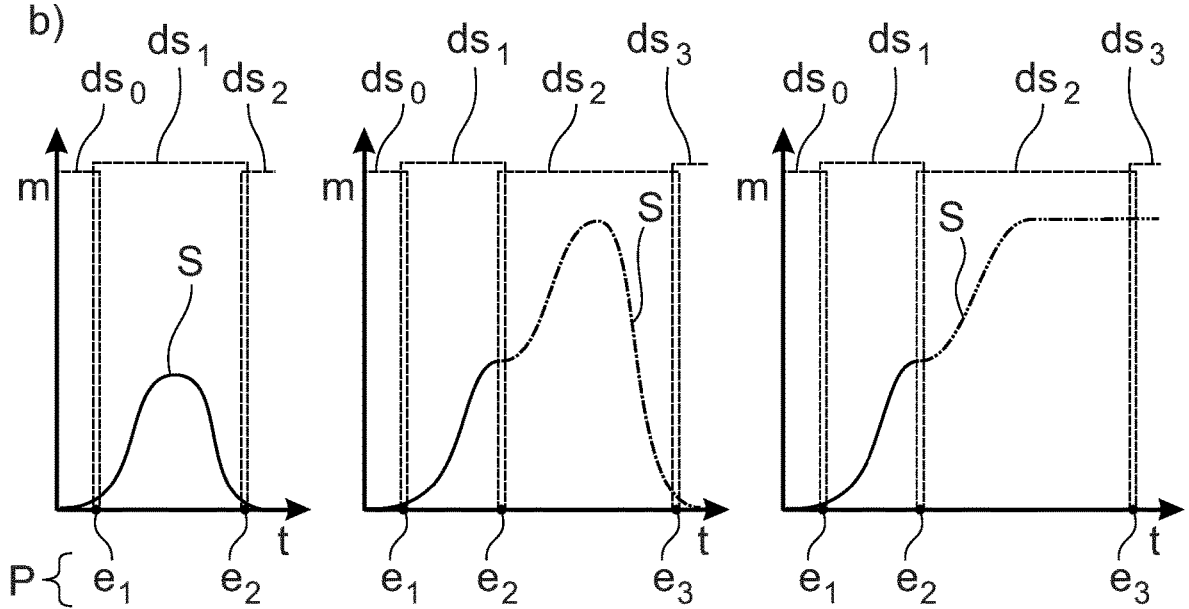
Figure 3:
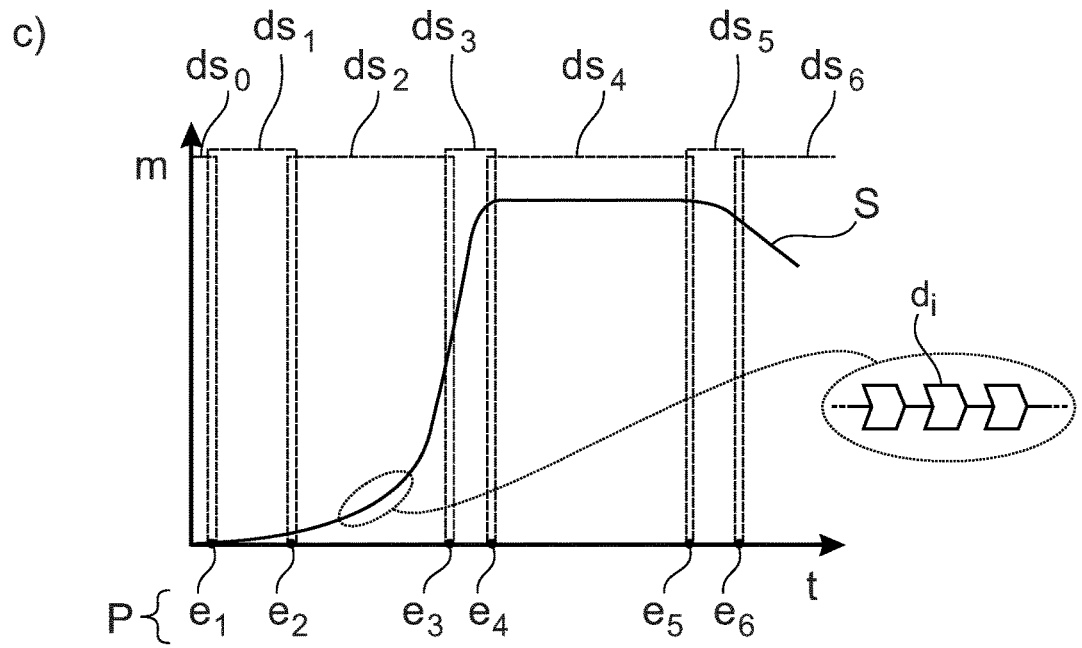

Each signing routine 24 can be based on an assigned bioprocess data set $ds_i$. These bioprocess data sets $ds_i$ are indicated in FIG. 3. FIG. 3b), 3c) and show, that here, subsequent bioprocess data sets $ds_i$, $ds_{i+1}$ are overlapping each other. In addition or as an alternative, an identifier of a respective previous bioprocess data set $ds_i$ may be added to the respective subsequent bioprocess dataset $ds_{i+1}$. In both cases, a certain redundancy is integrated into the bioprocess data set $ds_i$, that guarantees, that no data are being missed in the respective signing routine 24.

In some embodiments, the digital signature 26 generated by signing the documentation data 23 is received from the digital control unit 1 via the bioprocess interface 6 and stored in the local data storage 4. The digital control unit 1, as an alternative or in addition, may comprise a data transmission interface 28, wherein the digital control unit 1 transmits the digital signature 26 and/or the documentation data 23 and/or the bioprocess data 16 or parts of the respective data to an external data storage 29, which generally may be a process control system 30, which itself may well be another digital control unit. Here, the external data storage 29 is a so called "multifermenter" control system (MFCS), which comprises a local processor unit and a local data storage itself. The MFCS also provides a centralized process management system, dispatching requests to the digital control unit 1, which, however, does not play a role for this particular embodiment.

In order to further prevent a manipulation of bioprocess data 16, it can also be that after receipt by the digital control unit 1, the sensor data 12 and/or the user control command data 18 are protected from external manipulation. This may be done by control measures or by mechanical measures. The control measures may, for example, be a specific design of the control software and/or the safety software, such that access to the respective data is not possible via the user interface 17. Mechanical measures in this sense are to design the digital control unit 1 altogether in a mechanically robust fashion.

In the bioprocess control routine 19, as noted above, the digital control unit 1 generates the bioprocess data 16 based on the sensor data 12 and/or the actuator data 8 and/or the user control command data 18. According to the easiest approach, those data are sequentially arranged based on specific rules, that define, which of those data are to be assigned to the documentation data 23. In some embodiments, each data item of the bioprocess data 16 comprises at least the above noted, individual time stamp, a data item name and a data item value.

Generally it can be that the generation of the bioprocess data 16 is done continuously, such as periodically, with a period defined with relation to time or data volume. In addition, the step of grouping the bioprocess data 16 into data blocks $d_i$ during the documentation routine 22 can be done continuously as well. Also the hashing of the data blocks $d_i$ during the documentation routine 22 can be performed continuously. This continuous generation of bioprocess data 16, grouping into data blocks $d_i$ and hashing is advantageous, as the time frame, in which manipulation of data is still possible, is narrowed to a minimum.

The digital control unit 1, as its core task, controls the bioprocess by communicating with the actuator 9, 10 and the sensor 13, 14, 15. For this, the digital control unit 1 is configured to execute a feedback routine for realizing a control loop as noted above thereby influencing the bioprocess. Such control loop may serve to keep certain sensor data 12 stable by controlling the actuator 9, 10 accordingly.

The proposed solution is particularly advantageous in a situation, in which bioprocess data, that have been generated in a biotechnological environment during the bioprocess, shall be transmitted from a sender to a recipient. As an example, at least the bioprocess data 16 as well as the digital signature 26, are being sent to the recipient. The sender may be the operator of the biotechnological environment, in which the respective bioprocess has been executed. The recipient may be a governmental organisation applying a compliance procedure to the bioprocess in question.

Based on the digital signature 26 of the of the documentation data 23, the recipient of the bioprocess data 16 is able to verify the integrity of these bioprocess data 16. For this, the public key, which corresponds to the cryptographic private key 25, has also to be made available to the recipient. The public key may be provided by the sender of the bioprocess data 16 via a point to point data connection to the recipient or using a trusted key infrastructure (TKI).

With the above noted public key, the recipient may decrypt the digital signature 26 to receive the documentation data 23, which may be the hash root h0 or the complete hash tree H shown in FIG. 4*a*). Now applying the respective hash function to the received bioprocess data 16 leads to a hash tree, which is called the "verification hash tree V" in the following and which is shown in FIG. 4*b*).

Figure 4:
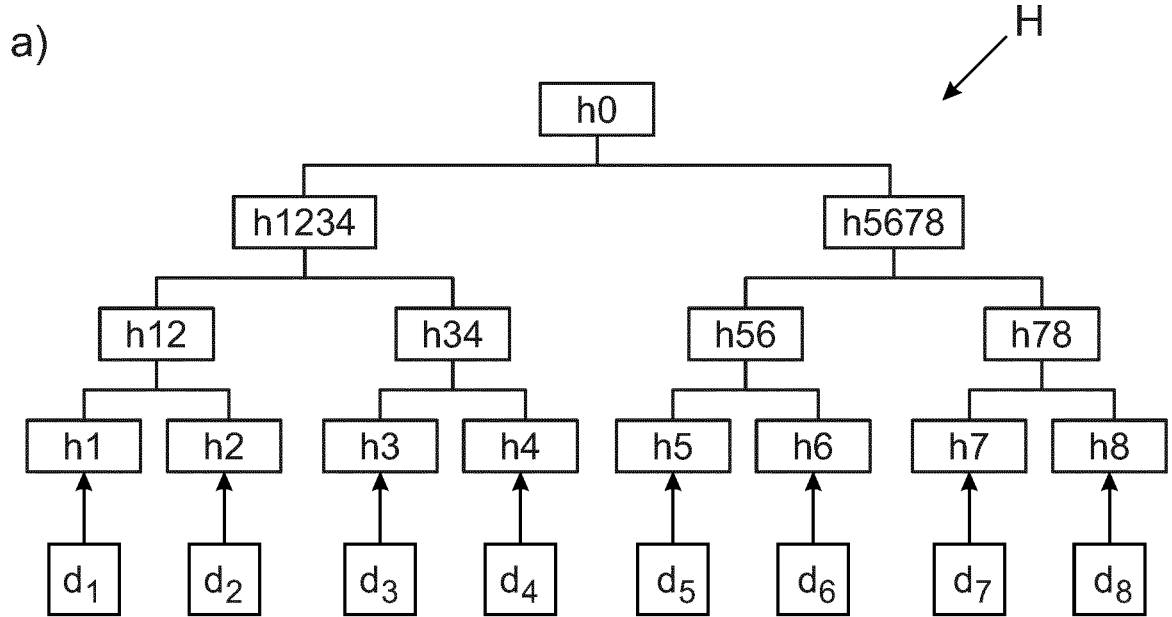
Figure 4:
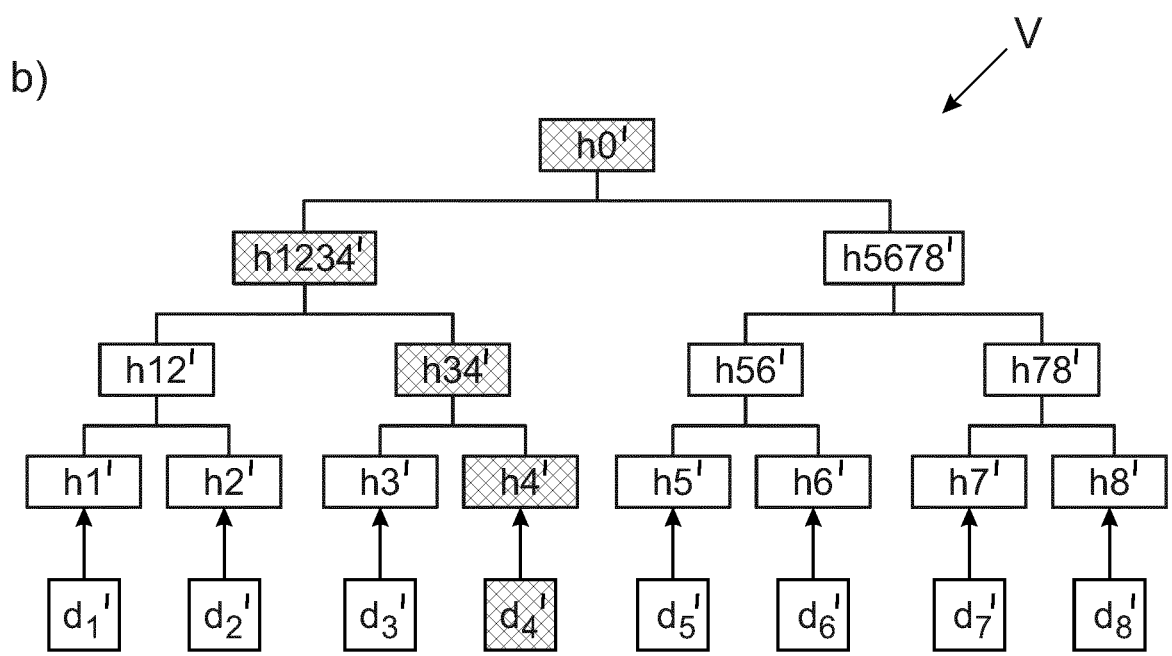

However, in the example shown in FIG. 4, the bioprocess data $d_4$ has been manipulated, which leads to the hashes h4', h34', h1234' and h0' being different from the hashes of the original hashes h4, h34, h1234 and h0. If the documentation data 23 are only based on the hash root h0, the recipient knows, that at least some data block $d_i$ is corrupted. If the documentation data 23 are only based on the complete hash tree H, the recipient may even derive by comparing the hash tree H to the verification hash tree V that data block $d_4$ is corrupted.

The above noted example shows, that by having the digital control unit 1 control the signing routine 24, verification of the data integrity is possible with high reliability and at the same time with high flexibility in terms of the signing process itself.

As indicated above, the data safety routine 21 may be executed in various ways on various hardware units, two of which are being pointed out in the following:

According to various embodiments, the whole data safety routine 21 is executed by the digital control unit 1. The private key data 20 are stored in the local data storage 4, wherein the data safety routine 21 is executed by the local processor unit 5, wherein the documentation routine 22 is executed by the local processor unit 5 in the data safety routine 21, wherein in the documentation routine 22, the documentation data 23 are generated from the bioprocess data 16 by the digital control unit 1. In this case, the signing routine 24 is executed by the local processor unit 5 in the data safety routine 21, wherein in the signing routine 24, a cryptographic private key 25 is extracted from the private key data 20 by the digital control unit 1 and wherein the documentation data 23 are signed with the cryptographic private key 25 by the digital control unit 1 by generating a digital signature 26.

According to various embodiments, at least the signing routine 24 is executed in an external unit, in particular the external signing unit s. Here, the private key data 20 are stored in the external signing unit s, wherein the data safety routine 21 is initiated by the local processor unit 5. The documentation routine 22 is then initiated by the local processor unit 5 in the data safety routine 21 to be executed by the local processor unit 5 or an external documentation unit d. In this documentation routine 22, the documentation data 23 are again generated from the bioprocess data 16 by the local processor unit 5 or the external documentation unit d, wherein the signing routine 24 is initiated by the local processor unit 5 in the data safety routine 21 to be executed by an external signing unit. In the signing routine 24, the cryptographic private key 25 is extracted from the private key data 20 by the external signing unit and that the documentation data 23 are digitally signed with the cryptographic private key 25 by generating a digital signature 26.

According to some embodiments, the digital control unit 1 is provided as such, which is configured to perform the proposed method. All explanations given before are fully applicable to this teaching.

According to another teaching, a control system with a proposed digital control unit 1 and an external documentation unit d and/or an external signing unit s is proposed as such. Again, reference is made to all explanations given before.

Finally, independent teachings are directed to the data processing system for the realization of the above noted method, can include the local data storage 4 and the local processor unit 5, to a computer program product for the data processing system and to a computer readable storage media, on which the computer program product is stored.

The invention claimed is:

1. A method for conducting a bioprocess with a digital control unit of a bioprocess arrangement,
   wherein the digital control unit comprises a local data storage and a local processor unit, wherein bioprocess data are generated by the digital control unit,
   wherein in a data safety routine, a documentation routine) and a signing routine are executed, that in the documentation routine, documentation data are generated from the bioprocess data and that in the signing routine, a cryptographic private key is extracted from private key data and the documentation data are digitally signed with the cryptographic private key by generating a digital signature,
   that the documentation routine is executed continuously during the bioprocess and that the signing routine is executed discontinuously during the bioprocess in several signing cycles according to a signing strategy, which defines trigger events for initiating the signing routine.

2. The method according to claim 1, wherein the digital control unit comprises a bioprocess interface for sending and receiving bioprocess control data, that the bioprocess interface comprises an actuator interface for sending actuator data to at least one actuator for influencing the bioprocess, that the bioprocess interface comprises a sensor interface for receiving sensor data related to the bioprocess from at least one sensor, that the digital control unit comprises a user interface for displaying to a user at least part of the bioprocess data and for receiving user control command data.

3. The method according to claim 2, wherein a bioprocess control routine is executed by the local processor unit to control the bioprocess, that in the bioprocess control routine, the sensor data are received by the digital control unit from the sensor, that in the bioprocess control routine, the actuator data are generated by the digital control unit based on the user control command data and/or the sensor data and the actuator is controlled by the digital control unit by sending the actuator data to the actuator thereby influencing the bioprocess, that in the bioprocess control routine, the bioprocess data are generated by the digital control unit from the actuator data and/or the sensor data and/or the user control command data.

4. The method according to claim 1, wherein at least one trigger event is defined as an event directly related to the bioprocess.

5. The method according to claim 1, wherein the bioprocess is assigned bioprocess steps and/or is assigned bioprocess phases and/or is assigned bioprocess states, and that at least one trigger event is defined with relation to at least one bioprocess step and/or at least one bioprocess phase and/or at least one bioprocess state.

6. The method according to claim 1, wherein at least one trigger event is defined in a time based manner.

7. The method according to claim 6, wherein at least one trigger event is defined as a point in time relative to a bioprocess step.

8. The method according to claim 6, wherein at least one trigger event is defined as a periodically repeating trigger event with a predefined period in terms of time.

9. The method according to claim 1, wherein at least one trigger event is defined based on a predefined change in the bioprocess phase and/or the bioprocess state.

10. The method according to claim 1, wherein at least one trigger event is defined based on a start or a termination of a bioprocess step or based on a start or a termination of a bioprocess phase.

11. The method according to claim 1, wherein at least one trigger event is defined based on the bioprocess control data.

12. The method according to claim 11, wherein, at least one trigger event is defined based on the sensor data and/or the user control command data and/or the actuator data.

13. The method according to claim 1, wherein the documentation routine comprises a step of grouping the bioprocess data into data blocks and a step of hashing the data blocks generating hashes of the data blocks and that the documentation data are generated from the hashes of the data blocks.

14. The method according to claim 13, wherein the documentation routine comprises a step of hashing the hashes of the data blocks in form of a tree structure into a hash root and that the documentation data are generated from the hash root.

15. The method according to claim 1, wherein during a single bioprocess the digital control unit continuously receives the sensor data from the sensor in the bioprocess control routine and continuously sends actuator data to the actuator thereby influencing the bioprocess.

16. The method according to claim 1, wherein each signing routine is based on an assigned bioprocess data set.

17. The method according to claim 16, wherein subsequent bioprocess data sets are overlapping each other, and/or, that an identifier of a respective previous bioprocess data set is added to the respective subsequent bioprocess data set.

18. The method according to claim 1, wherein the digital signature generated by signing the documentation data is received from the digital control unit via the bioprocess interface, and stored in the local data storage, and/or, that the digital control unit initiates the transmission of the digital signature and/or the documentation data and/or the bioprocess data or parts of the respective data to an external data storage via the data transmission interface.

19. The method according to claim 1, wherein the private key data are stored in the local data storage, that the data safety routine is executed by the local processor unit, that the documentation routine is executed by the local processor unit in the data safety routine, that in the documentation routine, the documentation data are generated from the bioprocess data by the digital control unit, that the signing routine is executed by the local processor unit in the data safety routine and that in the signing routine, cryptographic private key is extracted from the private key data by the digital control unit and that the documentation data are signed with the cryptographic private key by the digital control unit by generating a digital signature.

20. The method according to claim 1, wherein the private key data are stored in an external signing unit, that the data safety routine is initiated by the local processor unit, that the documentation routine is initiated by the local processor unit in the data safety routine to be executed by the local processor unit or an external documentation unit, that in the documentation routine, documentation data are generated from the bioprocess data by the local processor unit or the external documentation unit, that the signing routine is initiated by the local processor unit in the data safety routine to be executed by an external signing unit and that in the signing routine, a cryptographic private key is extracted from the private key data by the external signing unit and that the documentation data are digitally signed with the cryptographic private key by generating a digital signature.

21. A digital control unit of a bioprocess arrangement for controlling a bioprocess,
  wherein the digital control unit comprises a local data storage and a local processor unit,
  wherein the digital control unit comprises a bioprocess interface for sending and receiving bioprocess control data,
  wherein the bioprocess interface comprises an actuator interface for sending actuator data to at least one actuator for influencing the bioprocess,
  wherein the bioprocess interface comprises a sensor interface for receiving sensor data related to the bioprocess from at least one sensor,
  wherein the digital control unit generates bioprocess data,
  wherein the digital control unit comprises a user interface for displaying to a user at least part of the bioprocess data and for receiving user control command data,
  wherein the digital control unit is configured to execute a bioprocess control routine via the local processor unit to control the bioprocess,
  wherein in the bioprocess control routine, the digital control unit receives the sensor data from the sensor,
  wherein in the bioprocess control routine, the digital control unit generates the actuator data based on the user control command data and/or the sensor data and controls the actuator by sending the actuator data to the actuator thereby influencing the bioprocess,
  wherein in the bioprocess control routine, the digital control unit generates the bioprocess data from the actuator data and/or the sensor data and/or the user control command data,
  wherein private key data are stored in the local data storage unit or an external signing unit, that the digital control unit is configured to initiate a data safety routine via the local processor unit,
  that the digital control unit is configured to initiate a documentation routine via the local processor unit in the data safety routine to be executed by the local processor unit or an external documentation unit, that in the documentation routine, the local processor unit or the external documentation unit generates documentation data from the bioprocess data,
  that the digital control unit is configured to initiate a signing routine via the local processor unit in the data safety routine to be executed by the local processor unit or an external signing unit and that in the signing routine, the local processor unit or the external signing unit extracts a cryptographic private key from the private key data and digitally signs the documentation data with the cryptographic private key by generating a digital signature and that the documentation routine is executed continuously during the bioprocess and that the signing routine is executed discontinuously during the bioprocess in several signing cycles according to a signing strategy, which defines trigger events for initiating the signing routine and that the digital control unit is configured to initiate the signing routine discontinuously.

22. A non-transitory computer readable storage media, that has a computer program product that when executed performs the method according to claim 1.

* * * * *